(12) United States Patent
Sixto, Jr. et al.

(10) Patent No.: US 8,021,378 B2
(45) Date of Patent: Sep. 20, 2011

(54) SURGICAL CLIP

(75) Inventors: Robert Sixto, Jr., Miami, FL (US); Juergen A. Kortenbach, Miami Springs, FL (US); Thomas O. Bales, Coral Gables, FL (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1691 days.

(21) Appl. No.: 10/730,236

(22) Filed: Dec. 8, 2003

(65) Prior Publication Data
US 2004/0116948 A1 Jun. 17, 2004

Related U.S. Application Data

(63) Continuation of application No. 09/891,775, filed on Jun. 25, 2001, now Pat. No. 6,716,226.

(51) Int. Cl.
*A61B 17/08* (2006.01)
(52) U.S. Cl. .......................... 606/158; 24/543
(58) Field of Classification Search .................. 606/142, 606/143, 151, 157, 158; 24/543, 30.5 R; 227/902
See application file for complete search history.

(56) References Cited

U.S. PATENT DOCUMENTS

| | | | |
|---|---|---|---|
| 266,632 A | 10/1882 | Danforth | |
| 268,632 A | 12/1882 | Danforth | |
| 1,756,670 A | 4/1930 | Treat | |
| 2,246,495 A | 6/1941 | Alessi et al. | |
| 2,399,761 A | 5/1946 | Ruskin | |
| 3,851,359 A | 12/1974 | Wilson | |
| 4,038,987 A | 8/1977 | Komiya | 128/321 |
| 4,044,429 A | 8/1977 | Wagner | |
| 4,346,869 A | 8/1982 | MacNeill | |
| 4,390,019 A | 6/1983 | LeVeen et al. | |
| 4,418,694 A | 12/1983 | Beroff et al. | 128/326 |
| 4,430,997 A | 2/1984 | DiGiovanni et al. | |
| 4,444,187 A | 4/1984 | Perlin | 128/346 |
| 4,476,865 A | 10/1984 | Failla et al. | 128/326 |
| 4,512,345 A | 4/1985 | Green | |
| 4,519,392 A * | 5/1985 | Lingua | 606/151 |
| 4,572,181 A | 2/1986 | Mattler | 128/305 |
| 4,648,158 A * | 3/1987 | West | 24/23 W |
| 4,741,336 A | 5/1988 | Failla et al. | 128/334 |
| 4,800,879 A * | 1/1989 | Golyakhovsky et al. | 606/158 |
| 4,835,824 A | 6/1989 | Durham et al. | |
| 4,844,066 A | 7/1989 | Stein | |
| 4,934,364 A | 6/1990 | Green | |
| 4,988,355 A | 1/1991 | Leveen et al. | |
| 5,022,126 A | 6/1991 | Davis | |
| 5,030,226 A | 7/1991 | Green et al. | 606/158 |

(Continued)

*Primary Examiner* — Gary Jackson
*Assistant Examiner* — Eric Blatt
(74) *Attorney, Agent, or Firm* — Gordon & Jacobson, PC

(57) ABSTRACT

A surgical clip includes a U-shaped configuration with first and second arms, and a bridge portion therebetween. The first arm is provided with a tip preferably having a catch, and the second arm extends into a deformable retainer having a tissue-piercing end and preferably also a hook. During application, tissue is clamped, and the clip is forced over the clamped tissue and the retainer of the second arm is bent and may be pierced through the tissue. The retainer is toward and around or adjacent the tip of the first arm preferably until the hook is engaged about the catch to secure the clip to the tissue and prevent the clip and tissue from separating. The clip is provided with structure that facilitates the stacking of a plurality of clips in a clip chamber of a clip applier.

21 Claims, 4 Drawing Sheets

U.S. PATENT DOCUMENTS

| | | | | |
|---|---|---|---|---|
| 5,049,153 A | | 9/1991 | Nakao et al. | |
| 5,062,846 A | * | 11/1991 | Oh et al. | 606/158 |
| 5,099,827 A | | 3/1992 | Melzer et al. | |
| 5,156,609 A | | 10/1992 | Nakao et al. | 606/142 |
| 5,159,730 A | | 11/1992 | Radvin | |
| 5,160,339 A | * | 11/1992 | Chen et al. | 606/158 |
| 5,163,945 A | | 11/1992 | Ortiz et al. | 606/142 |
| 5,171,249 A | | 12/1992 | Stefanchik et al. | 606/142 |
| 5,174,276 A | | 12/1992 | Crockard | 128/4 |
| 5,207,692 A | | 5/1993 | Kraus et al. | |
| 5,222,961 A | | 6/1993 | Nakao et al. | 606/143 |
| 5,271,543 A | | 12/1993 | Grant et al. | 227/179.1 |
| 5,312,426 A | | 5/1994 | Segawa | 606/158 |
| 5,354,306 A | | 10/1994 | Garvey et al. | 606/157 |
| 5,361,463 A | | 11/1994 | Revis | |
| 5,366,459 A | | 11/1994 | Yoon | 606/151 |
| 5,383,880 A | | 1/1995 | Hooven | 606/142 |
| 5,395,030 A | | 3/1995 | Kuramoto et al. | 227/179.1 |
| 5,403,326 A | | 4/1995 | Harrison et al. | 606/139 |
| 5,409,499 A | * | 4/1995 | Yi | 606/151 |
| 5,425,740 A | | 6/1995 | Hutchinson | 606/157 |
| 5,433,721 A | | 7/1995 | Hooven et al. | 606/143 |
| 5,439,468 A | | 8/1995 | Schulze et al. | 606/143 |
| 5,439,479 A | | 8/1995 | Shichman et al. | |
| 5,441,509 A | | 8/1995 | Vidal et al. | 606/151 |
| 5,445,167 A | | 8/1995 | Yoon et al. | |
| 5,464,416 A | | 11/1995 | Steckel | 606/158 |
| 5,474,570 A | | 12/1995 | Kockerling et al. | |
| 5,482,054 A | | 1/1996 | Slater et al. | 128/751 |
| 5,487,746 A | | 1/1996 | Yu et al. | 606/151 |
| 5,497,933 A | | 3/1996 | DeFonzo et al. | 227/175.1 |
| 5,501,693 A | | 3/1996 | Gravener | |
| 5,522,823 A | | 6/1996 | Kuntz | 606/157 |
| 5,562,694 A | | 10/1996 | Sauer et al. | 606/176 |
| 5,571,116 A | | 11/1996 | Bolanos et al. | 606/139 |
| 5,575,802 A | | 11/1996 | McQuilkin et al. | |
| 5,582,617 A | | 12/1996 | Klieman et al. | 606/170 |
| 5,601,573 A | | 2/1997 | Fogelberg et al. | 606/143 |
| 5,626,585 A | | 5/1997 | Mittelstadt et al. | |
| 5,632,753 A | | 5/1997 | Loeser | 606/151 |
| 5,657,519 A | | 8/1997 | Smith | |
| 5,667,517 A | | 9/1997 | Hooven | 606/151 |
| 5,673,841 A | | 10/1997 | Schulze et al. | 227/175.1 |
| 5,681,330 A | | 10/1997 | Hughett et al. | 606/143 |
| 5,722,421 A | | 3/1998 | Francese et al. | 128/751 |
| 5,741,283 A | | 4/1998 | Fahy | 606/157 |
| 5,766,189 A | | 6/1998 | Matsuno | 606/158 |
| 5,769,857 A | | 6/1998 | Reztzov et al. | |
| 5,775,345 A | | 7/1998 | Chou | |
| 5,779,718 A | | 7/1998 | Green et al. | 606/143 |
| 5,792,150 A | | 8/1998 | Pratt et al. | 606/143 |
| 5,800,449 A | | 9/1998 | Wales | 606/172 |
| 5,817,116 A | * | 10/1998 | Takahashi et al. | 606/167 |
| 5,833,695 A | | 11/1998 | Yoon | 606/139 |
| 5,833,700 A | * | 11/1998 | Fogelberg et al. | 606/158 |
| 5,858,018 A | | 1/1999 | Shipp et al. | 606/142 |
| 5,891,156 A | | 4/1999 | Gessner et al. | |
| 5,897,507 A | | 4/1999 | Kortenbach et al. | 600/562 |
| 5,904,693 A | | 5/1999 | Dicesare et al. | 606/143 |
| 5,906,630 A | | 5/1999 | Anderhub et al. | 606/205 |
| 5,937,488 A | | 8/1999 | Geiger | |
| 5,941,439 A | | 8/1999 | Kammerer et al. | 227/67 |
| 5,993,465 A | | 11/1999 | Shipp et al. | 606/142 |
| 5,993,476 A | | 11/1999 | Groiso | 606/219 |
| 6,001,110 A | | 12/1999 | Adams | |
| 6,086,600 A | | 7/2000 | Kortenbach | 606/139 |
| 6,099,537 A | | 8/2000 | Sugai et al. | 606/143 |
| 6,139,555 A | | 10/2000 | Hart et al. | 606/139 |
| 6,149,658 A | | 11/2000 | Gardiner et al. | |
| 6,149,660 A | | 11/2000 | Laufer et al. | 606/143 |
| 6,159,223 A | | 12/2000 | Danks et al. | 606/142 |
| 6,162,233 A | | 12/2000 | Williamson, IV et al. | |
| 6,231,581 B1 | * | 5/2001 | Shank et al. | 606/157 |
| 6,269,819 B1 | | 8/2001 | Oz et al. | |
| 6,352,503 B1 | | 3/2002 | Matsui et al. | |
| 6,387,041 B1 | | 5/2002 | Harari et al. | |
| 6,423,079 B1 | | 7/2002 | Blake, III | |
| 6,425,900 B1 | | 7/2002 | Knodel et al. | |
| 6,517,555 B1 | | 2/2003 | Caro | |
| 6,560,488 B1 | | 5/2003 | Crawford | |
| 6,578,759 B1 | | 6/2003 | Ortiz | |
| 6,613,059 B2 | * | 9/2003 | Schaller et al. | 606/157 |
| 6,716,226 B2 | | 4/2004 | Sixto, Jr. et al. | 606/157 |
| 6,843,794 B2 | | 1/2005 | Sixto, Jr. et al. | |
| 6,945,979 B2 | | 9/2005 | Kortenbach et al. | |
| 6,960,221 B2 | * | 11/2005 | Ho et al. | 606/157 |
| 7,001,412 B2 | * | 2/2006 | Gallagher et al. | 606/232 |
| 7,070,602 B2 | | 7/2006 | Smith et al. | |
| 7,090,685 B2 | | 8/2006 | Kortenbach et al. | |
| 2001/0056282 A1 | | 12/2001 | Sonnenschein et al. | |
| 2002/0082621 A1 | | 6/2002 | Schurr et al. | |
| 2002/0104199 A1 | | 8/2002 | Chen | |
| 2002/0111641 A1 | * | 8/2002 | Peterson et al. | 606/157 |
| 2002/0198538 A1 | | 12/2002 | Kortenbach et al. | |
| 2002/0198549 A1 | | 12/2002 | Sixto et al. | |
| 2005/0107809 A1 | | 5/2005 | Litscher et al. | |

* cited by examiner

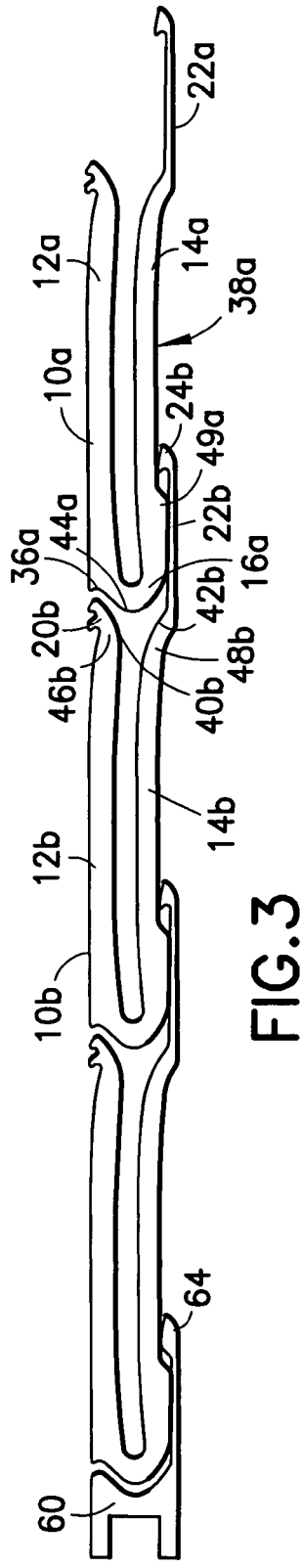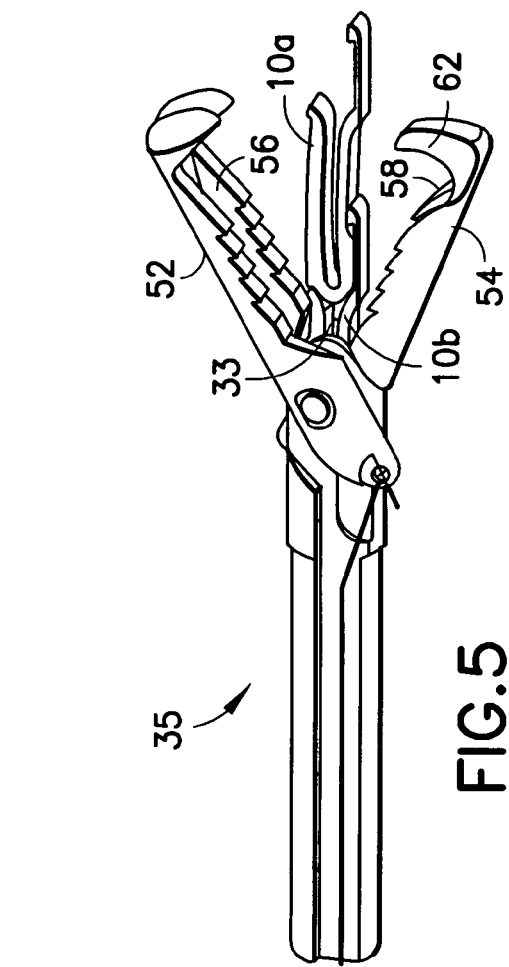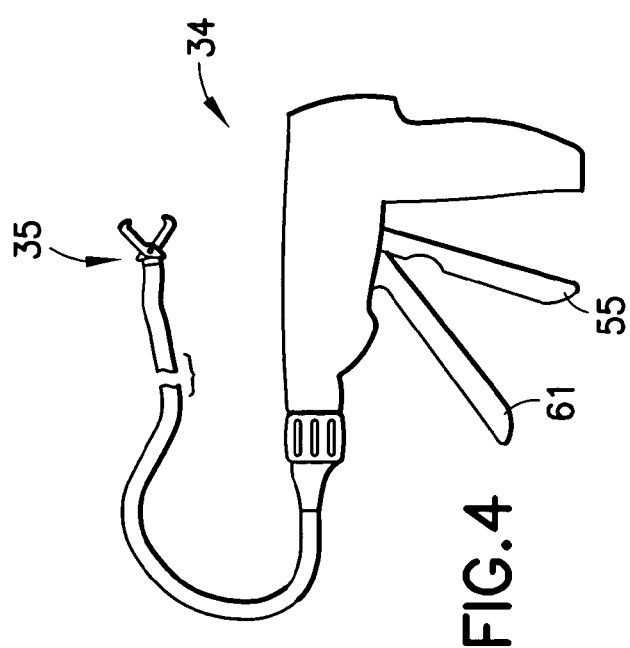
FIG.3
FIG.4
FIG.5

SURGICAL CLIP

This application is a continuation of U.S. Ser. No. 09/891,775, filed Jun. 25, 2001, which issued on Apr. 6, 2004, as U.S. Pat. No. 6,716,226.

BACKGROUND OF THE INVENTION

1. Field of the Invention

This invention relates broadly to surgical devices. More particularly, this invention relates to a surgical clip for clamping and/or suturing, ducts, vessels, and other tissues, for anchoring a tissue, or for attaching a foreign body to a tissue.

2. State of the Art

Surgical clips are generally used to apply clamping force to ducts, vessels, and other tissues. In addition, surgical clips are particularly useful in controlling bleeding of a tissue in lieu of suturing or stapling where suturing or stapling is difficult. However, in certain circumstances, the bleeding tissue is lubricous, and applied clips often slip from the tissue and are dislodged, removing the necessary clamping force thereabout. This is particularly a problem when a clip is provided about tissue which is not a conduit of a size which can be completely surrounded by the clip. For example, it is very difficult to secure a clip about a small peripheral portion of ulcerated stomach tissue and therefore it is difficult to effect hemostasis of such bleeding tissue with a clip. Moreover, the problem is amplified when the clip used is very small.

In order to prevent dislodgement, a combination of a clip and a staple has been described in U.S. Pat. No. 5,522,823 to Kuntz et al. In the Kuntz clip, one end portion of the clip is pierced through the tissue and captured in an eye of another end portion of the clip to secure the clip on the tissue. With the clip piercing the tissue, the likelihood that the clip will become inadvertently dislodged is greatly reduced.

While the Kuntz et al. clip represents a step forward, the disclosed clip is not particularly useful in endoscopic procedures. In particular, both the nature of the clip and the manner in which it is applied are complex. For example, in order to facilitate the bending of the clip through various configurations required of its applier, the clip has portions provided with at least four different widths as well as an eye opening. This complex clip structure is not practical for a clip which is to be used in a flexible endoscopy procedure in which the tools used are of very small diameter, e.g., 2-6 mm (0.08-0.24 inch). In addition, for endoscopic procedures it is highly desirable that multiple clips be able to be applied without removing the clip applier from its general location. The Kuntz et al. clip and applier, however, are not particularly adapted for applying multiple clips, as the Kuntz et al. clip does not stack, and the applier with which it is used holds a single clip at a time.

SUMMARY OF THE INVENTION

It is therefore an object of the invention to provide a surgical clip which remains secured to the tissue to which it is applied.

It is another object of the invention to provide a surgical clip which pierces tissue in order to maintain a secure hold on the tissue to which it is applied.

It is a further object of the invention to provide a surgical clip which is adapted for use in minimally invasive surgery.

It is an additional object of the invention to provide a surgical clip which can be applied in a flexible endoscopy setting.

It is also an object of the invention to provide a surgical clip which can be used with rigid instruments operated through a port in the human body.

It is yet another object of the invention to provide a surgical clip which can be used in open surgery.

It is still a further object of the invention to provide a surgical clip which is relatively easy to manufacture.

It is still another object of the invention to provide a surgical clip which is particularly adapted for use in an applier which holds a plurality of clips.

In accord with these objects, which will be discussed in detail below, a surgical clip is provided having a generally U shaped configuration with first and second arms, and a bridge portion therebetween. The first arm is provided with a tip preferably having one or more catches, and the second arm extends into a deformable retainer preferably having a tissue-piercing end and preferably also a hook. During application, the clip is forced over compressed tissue. As the clip is forced over the tissue, the retainer of the second arm is bent and may pierce through the tissue. The retainer is preferably sized to be bent sufficiently toward and around the tip of the first arm until the hook engages in one of the catches to secure the clip to the tissue and prevent the clip and tissue from separating. In other embodiments, the clip includes neither the hook nor the catch; the retainer is simply bent to pierce the tissue and preferably folded about the tip of the first arm to prevent the clip and tissue from separating. In yet another embodiment, the clip includes a plurality of retainers which are bent to aid in securing the clip to or about tissue.

According to a preferred aspect of the invention, the clip is provided with structure that facilitates the stacking (or chaining) of a plurality of clips in a clip chamber of an applier. The structure includes: a notch at a junction of the first arm and the bridge portion which is adapted to receive the tip of the first arm of another clip; an elongate recess along the exterior of the second arm which is adapted to receive the retainer of the second arm of another clip; and an interior configuration at the ends of the first and second arms which corresponds to an exterior portion of the bridge portion of another clip. The recess on the second arm may be provided adjacent the bridge portion or between a rear portion of the second arm and the retainer thereof.

Additional objects and advantages of the invention will become apparent to those skilled in the art upon reference to the detailed description taken in conjunction with the provided figures.

BRIEF DESCRIPTION OF THE DRAWINGS

FIG. 3 is a schematic of a plurality of stacked surgical clips according to the invention;

FIG. 4 is a broken side elevation of a flexible endoscopic clip applier used to apply the surgical clips of the invention to tissue;

FIG. 5 is an enlarged partial section of the distal end of the clip applier of FIG. 4;

DETAILED DESCRIPTION OF THE PREFERRED EMBODIMENTS

Figure 1:
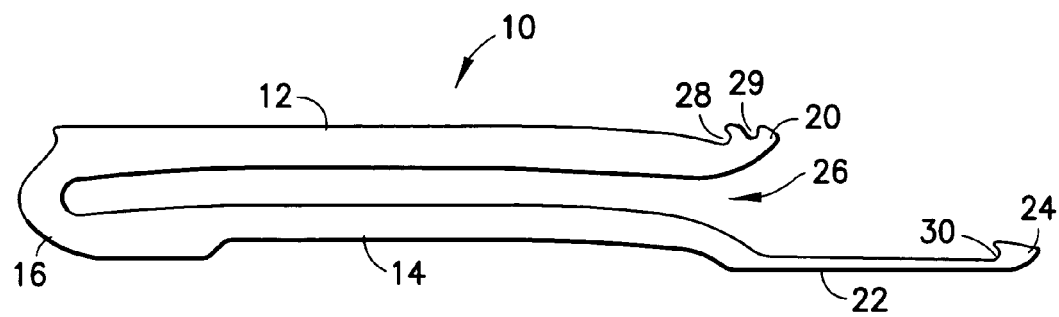
FIG. 1 is a side elevation of a first embodiment of a surgical clip according to the invention, shown in a pre-use configuration.
Figure 2:
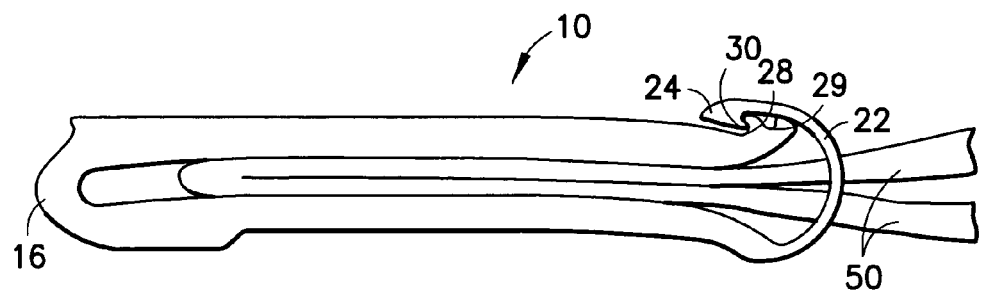
FIG. 2 is a side elevation of the first embodiment of the surgical clip according to the invention shown secured on tissue.

Turning now to FIGS. 1 and 2, a surgical clip 10 includes first and second arms 12, 14, respectively, and a bridge portion 16 therebetween such that the arms and bridge portion are in a generally U-shaped configuration. The first arm 12 is provided with an end 20, and the second arm 14 extends (or transitions) into a deformable retainer 22 preferably having a tissue piercing tip 24. The clip 10 is preferably made from a unitary piece of titanium, titanium alloy, stainless steel, tantalum, platinum, other high Z (substantially radiopaque) materials, nickel-titanium alloy, martensitic alloy, or plastic, although other suitable biocompatible materials may be used. The first and second arms 12, 14 extend in a substantially parallel direction, with the arms and the bridge defining a generally U-shape. The first and second arms 12, 14, as well as the bridge portion 16 are relatively stiff and preferably elastically deformable within the limits of force applied to the arms during use, while the retainer 22 is relatively easily plastically deformable by a clip applier, as briefly described hereafter.

The retainer 22 is sized to be bent across the opening 26 between the first and second arms 12, 14 and about the end 20 of the first arm 12. The retainer preferably has a length 0.7 to 2 times the height of the staple (measured from the outer side of the first arm to the outer side of the second arm). The retainer 22 has a preferred approximate thickness of 0.002-0.020 inch, and preferably tapers down in thickness toward its tip. The overall thickness of an arm is preferably 0.002 inch to 0.080 inch. The overall width of the staple is preferably 0.005 inch to 0.100 inch.

According to a preferred first embodiment, the end 20 of the first arm 12 is provided with one or more catches, e.g., catches 28 and 29, and the tissue piercing tip 24 is provided with a hook 30 which is adapted to engage the catches 28, 29 (FIG. 2).

Referring to FIGS. 1 and 3 (wherein letter subscripts are used to denote like parts on distinct like clips), according to a preferred aspect of the invention, the clip 10 is provided with structure that facilitates the stacking (or chaining) of a plurality of clips in a chamber 33 at the distal end 35 of a clip applier 34 (FIG. 4). The structure includes: a notch 36a at the junction of the first arm 12a and the bridge portion 16a, which is adapted to receive the end 20b of the first arm 12b of a second clip 10b; an elongate recess 38a along the exterior of the second arm 14a, adapted to receive the tip 24b of the retainer 22b of the second arm 14b of the second clip 10b; and an interior portion 40b, 42b of each of the first and second arms 12b, 14b, which has a shape which corresponds to an exterior portion 44a of a bridge portion 16a of a first clip 10a.

The corresponding interior portions 40b, 42b are preferably defined by slight outward bends 46b, 48b, or an internal flaring, in the first and second arms. According to the first embodiment, the recess 38a is located between a rear portion 49a of the second arm 14a and the retainer 12a thereof.

Referring to FIGS. 4 and 5, the clips are particularly suitable for use in a flexible endoscopic clip applier (although they may be used in rigid instruments in both laparoscopic and open surgery), as the clips may be manufactured in the small sizes necessary for such minimally invasive procedures, e.g., 0.04-0.08 inch (1-2 mm) across the first and second arms. Prior to use, a plurality of clips, e.g., 10a, 10b, are positioned in the above described stacked configuration in the chamber 33 of the clip applier 34. During application, and referring to FIGS. 2, 4 and 5, the jaws 52, 54 of the clip applier 35 are clamped (by operation of a first handle 55) about the tissue 50 over which the clip 10a is to be applied. The tissue is thereby compressed. The jaws 52, 54 include grooves 56, 58 through which the arms 12, 14 of a clip can be pushed. With the tissue compressed by the jaws, the clips are pushed distally by an arm 60 (FIG. 3) at the rear of the chamber 33 until the arms 12a, 14a of the distalmost clip 10a are forced over the compressed tissue. The arm 60 is attached to a pushwire, coil, tube, or other structure (not shown) which is moved relative to the chamber 33 by a second handle 61 on the clip applier (FIG. 5). As the clip 10 is pushed through the grooves 56, 58 over the tissue 50, the retainer 22 of the second arm 14 contacts an anvil 62 at the end of jaw 54 which bends (plastically deforms) the retainer and pushes the retainer toward and around (or at least adjacent) the end 20 of the first arm, preferably until the hook 30 of the tip 24 is engaged about a catch, e.g., catch 28, to secure the clip to the tissue 50 (FIG. 2). If the clip is provided over a portion of tissue which, as a whole, is relatively larger than the space between the arms of the clip, as the retainer is bent by the anvil it will likely pierce the tissue. As the arms 12, 14 and bridge 16 are relatively stiff, the arms and bridge retain their shape and are not plastically deformed during application over tissue. That is, any expansion of the clip between the arms is minimal and elastic.

After a clip is deployed, the other clips in the chamber are preferably retracted back into the chamber to reset the clip applier in preparation for subsequent clip application. The recess 38 on the clips provides a structure by which the clips may be engaged and maneuvered proximally within the chamber via a retention portion 64 of the arm 60 (FIG. 3).

Figure 6:
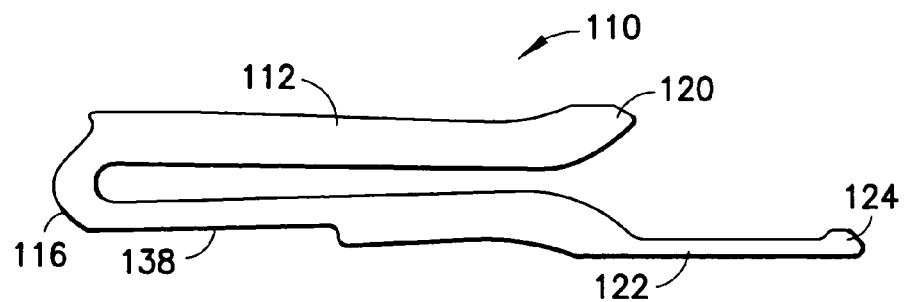
FIG. 6 is side elevation of a second embodiment of a surgical clip according to the invention, shown in a pre-use configuration.

Turning now to FIG. 6, a second embodiment of the surgical clip 110, substantially similar to the first embodiment (with like parts having numbers incremented by 100), is shown. The end 120 of the first arm 112 of the clip 110 does not include a defined catch, although it does extend outwardly. The tip 124 of the retainer 122, consequently, does not include a hook, but preferably is enlarged. When the retainer 122 is bent about the end of the first arm, the enlarged tip 124 rests against the back of the outwardly extending end 120. When the retainer 122 is bent or folded over the end of the first arm 112, approximately 0.3-1.0 lb of force (for relatively small clips) is required to straighten (i.e., plastically deform) the clip from its closed configuration. In addition, the recess 138 on the second arm is provided adjacent the bridge portion 116 and permits stacking of like clips. Providing the recess 138 in such a manner permits a mechanism (not shown) on a clip applier to apply distal force to a clip or clip stack within a clip chamber, but does not facilitate proximal movement of the clip or stack via engagement at the recess.

Figure 7:
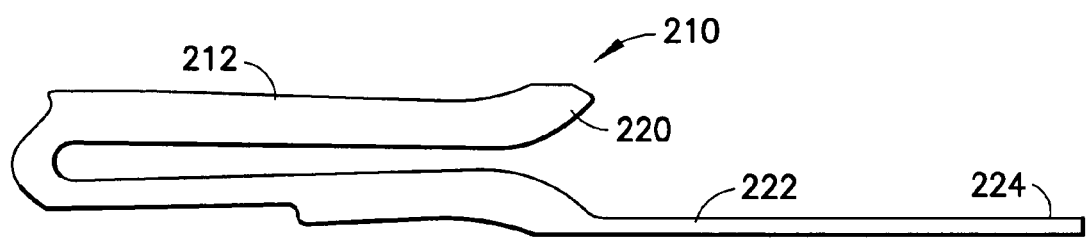
FIG. 7 is side elevation of a third embodiment of a surgical clip according to the invention, shown in a pre-use configuration.

Turning now to FIG. 7, a third embodiment of the surgical clip 210, substantially similar to the first embodiment (with like parts having numbers incremented by 200), is shown. The tip 224 of the retainer 222 does not include any enlargement, but is rather designed to be partially bent to pierce the tissue and then be further bent substantially about the end 220 of the first arm 212 in order to secure the clip on tissue.

Figure 8:
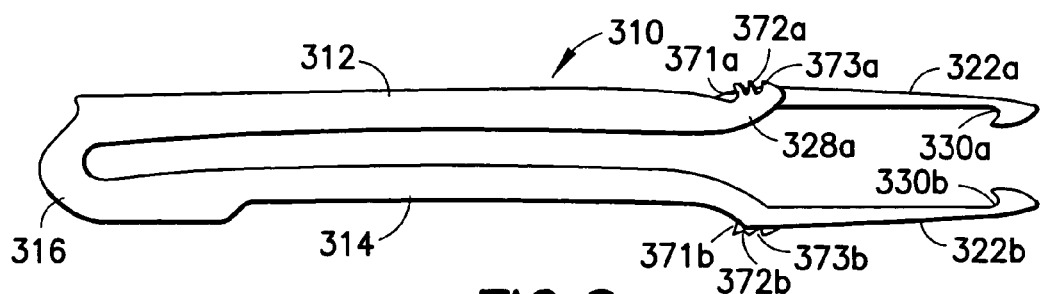
FIG. 8 is a side elevation of a fourth embodiment of a surgical clip according to the invention, shown in a pre-use configuration.
Figure 9:
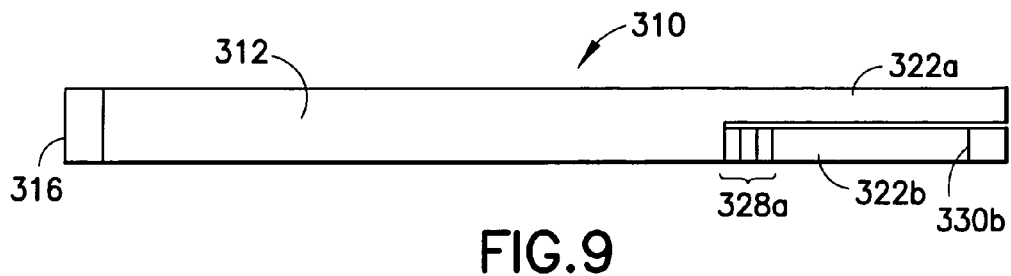
FIGS. 9 and 10 are top and bottom views, respectively, of the fourth embodiment of a surgical clip according to the invention, shown in a pre-use configuration.
Figure 10:
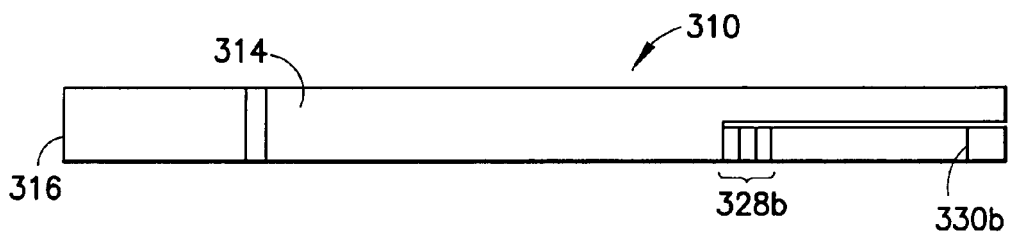

Turning now to FIGS. 8 through 10, a fourth embodiment of the surgical clip 310, substantially similar to the first embodiment (with like parts having numbers incremented by 300), is shown. The clip 310 includes first and second arms 312, 314 and a bridge 316, as in the previous embodiments. The first arm 312 includes both a catch portion 328a and a retainer portion 322a. The second arm 314 also includes both a catch portion 328b and a retainer portion 322b. The retainer and catch portions are offset such that retainer portion 322a is adapted to be bent toward catch portion 328b, with the hook 330a engaging the catch portion, and retainer portion 322b is adapted to be bent toward catch portion 328a for similar engagement. The catch portions 328a, 328b are shown with three catches 371a, 372a, 373a and 371b, 372b, 373b, respectively. Multiple catches facilitate a locked closing in different positions.

Figure 11:
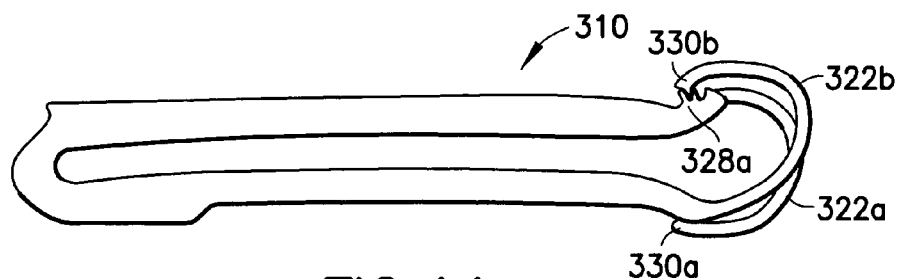
FIG. 11 is a side elevation of the fourth embodiment of a surgical clip according to the invention, shown in a post-use configuration.
Figure 12:
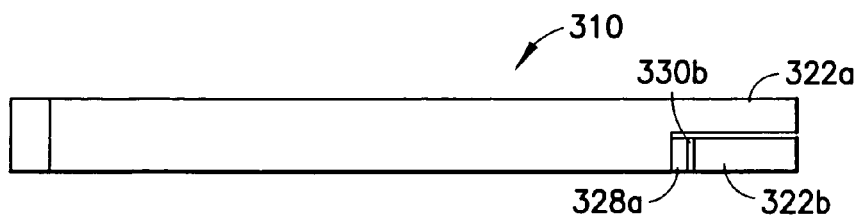
FIG. 12 is top view of the fourth embodiment of a surgical clip according to the invention, shown in a post-use configuration.

Such a clip is deployed in the same manner as the clip of the first embodiment, but the jaw assembly of the clip applier includes anvils at the ends of both of the jaws (not shown) to effect the bending and folding of the retainer portions 322a, 322b. In this manner, the hooks 330a, 330b at the end of the retainer portion engage the catch portions 328a, 328b, as shown in FIGS. 11 and 12.

While the clips are described as being adapted to pierce tissue, it is recognized that the clips may be applied over a duct, vessel, or other conduit or tissue which the clips completely surrounds such that the clips are clamped thereon but do not pierce the tissue thereof. In such use, the clamping force of the clips retains the clips over the tissue. Furthermore, the clips can be used to clamp a first tissue and pierce a second tissue to secure the first and second tissues together, e.g., as in a stitch. Moreover, the clips can be used to attach a foreign body to tissue.

There have been described and illustrated herein several embodiments of a surgical clip and a method of using the same. While particular embodiments of the invention have been described, it is not intended that the invention be limited thereto, as it is intended that the invention be as broad in scope as the art will allow and that the specification be read likewise. Thus, while the clip is particularly adapted for manufacture in the small size necessary for flexible endoscopy, it will be appreciated that the clip may be made in other sizes as well. In addition, while in one embodiment the retainer tip includes a hook and the end of the first arm is provided with a catch, it will be appreciated that the retainer tip may have a catch and the first arm may have a hook. In addition, other engagement means may be used. Also within the scope of the invention are other clip configurations with more than two retainers, and preferably more than two catches. The retainers and catches may be provided on the same arm, or alternatively, all the retainers may be on one arm, while all the catches are all provided on the other arm. Furthermore, in a multi-retainer embodiment, it is not necessary to have any catches, as described with respect to the second and third embodiments. It will therefore be appreciated by those skilled in the art that yet other modifications could be made to the provided invention without deviating from its spirit and scope as claimed.

What is claimed is:

1. A surgical clip for use on a patient, comprising:
a) a first arm portion having a tip, a first opposite end, a first inwardly facing surface, and a first outwardly facing surface, said first arm portion defining a thickness between said first inwardly facing surface and said first outwardly facing surface, a first length between said tip and said first opposite end, and a first width which is transverse to said first length and said thickness of said first arm portion;
b) a second arm portion having a first end, a second opposite end, a second inwardly facing surface, and a second outwardly facing surface, said second arm portion defining a thickness between said second inwardly facing surface and said second outwardly facing surface, a second length between said first and second ends of said second arm portion, and a second width which is transverse to said second length and said thickness of said second arm portion;
c) a retainer extending from said first end of said second arm portion, said retainer having a width which is identical to and parallel with said second width of said second arm portion, and a tissue piercing tip; and
d) a bridge portion connecting said opposite ends of said first and second arm portions,
wherein said first and second arm portions and said bridge portion comprise a single continuous piece of material, and
wherein
i) said clip is configurable to an original first configuration in which said retainer extends beyond said tip of said first arm portion substantially parallel to said first and second arm portions,
ii) said clip is configurable to an applied second configuration in which said tissue piercing tip of said retainer is disposed about or adjacent said tip of said first arm portion,
iii) said retainer is adapted to plastically deform from its orientation in said original first configuration to its orientation in said applied second configuration, and
iv) said first and second arm portions and said bridge portion are substantially stiff to maintain a generally U-shaped configuration in which said bridge portion extends through at least 90 degrees and said first and second arm portions are substantially parallel to each other in said original first and applied second configurations, and while said retainer is plastically deformed between said original first and applied second configurations.

2. A surgical clip according to claim 1, wherein:
said clip is made from titanium or a titanium alloy.

3. A surgical clip according to claim 1, wherein:
said clip is made from one of stainless steel, tantalum, platinum, a radiopaque material, a nickel-titanium alloy, a martensitic alloy, and a plastic.

4. A surgical clip for use on a patient, comprising:
a) a first arm portion having a tip end provided with one of a hook portion and a catch portion, and an opposite end;
b) a second arm portion having a first end and an opposite end;
c) a retainer extending from said first end and having the other of said hook portion and said catch portion; and
d) a bridge portion connecting said opposite ends of said first and second arm portions,
wherein said first and second arm portions and said bridge portion comprise a single continuous piece of material and
wherein,
(i) said clip is configurable to an original first configuration in which said retainer extends beyond said tip end of said first arm portion substantially parallel to said first and second arm portions,
(ii) said clip is configurable to an applied second configuration in which said other of said hook portion and said catch portion of said retainer is disposed about or adjacent said one of said hook portion and said catch portion of said first arm portion, (iii) said retainer is adapted to plastically deform from its orientation in said original first configuration to its orientation in said applied second configuration, and iv) said first and second arm portions and said bridge portion are substantially stiff to maintain a generally U-shaped configuration in which said first and second arm portions are substantially parallel to each other in said original first configuration and while said retainer is plastically deformed between said original first and second applied configurations.

5. A surgical clip according to claim 4, wherein:
said other of said hook portion and said catch portion is adapted to engage said one of said hook portion and said catch portion in said applied second configuration.

6. A surgical clip for use on a patient, comprising:
a) a first arm portion having a tip, a first opposite end, a first inwardly facing surface, and a first outwardly facing surface, said first arm portion defining a thickness between said first inwardly facing surface and said first outwardly facing surface, a first length between said tip and said first opposite end, and a first width which is transverse to said first length and said thickness of said first arm portion;
b) a second arm portion having a retainer extending therefrom beyond said tip of said first arm portion and a second opposite end, said retainer being deformably bendable and having a tip portion, said second arm portion having a second inwardly facing surface, a second outwardly facing surface, and defining a thickness between said second inwardly facing surface and said second outwardly facing surface, a second length between said tip and said second opposite end, and a second width which is transverse to said second length and said thickness of said second arm portion; and
c) a bridge portion connecting the first and second opposite ends of said first and second arm portions,
wherein said clip is configurable to an original first configuration in which said retainer extends substantially parallel to both said first and second arm portions, and an applied second configuration in which said tip portion of said retainer is bent around or adjacent said tip of said first arm portion,
wherein said first and second arm portions and said bridge portion of said clip are substantially stiff to maintain a generally U-shaped configuration in which said first and second arm portions are substantially parallel to each other in said original first configuration and while said retainer is plastically deformed between said original first and applied second configurations, and
wherein, said inwardly facing surfaces of said first and second arm portions face each other and said outwardly facing surfaces of said first and second arm portions are offset from each other by no more than 2 mm.

7. A surgical clip according to claim 6, wherein:
said tip portion is adapted to pierce tissue.

8. A surgical clip for use on a patient, comprising:
a) a first arm portion having a tip and a first opposite end;
b) a second arm portion having a transition portion and a second opposite end,
c) a plastically deformable retainer portion provided at the transition portion and extending therefrom beyond said tip of said first arm portion; and
d) a bridge portion connecting the first and second opposite ends, wherein said first and second arm portions and said bridge portion comprise a single continuous piece of material and are substantially stiff to maintain a generally U-shaped configuration in which said first and second arm portions are substantially parallel to each other during application of said clip to tissue of the patient and wherein, said first arm portion defines a first inwardly facing surface and a first outwardly facing surface opposite said first inwardly facing surface, said second arm portion defines a second inwardly facing surface and a second outwardly facing surface opposite said second inwardly facing surface, and said outwardly facing surfaces of said first and second arm portions are offset from each other by no more than 2 mm.

9. A surgical clip according to claim 8, wherein:
said clip is made from titanium or titanium alloy.

10. A surgical clip according to claim 8, wherein:
said clip is made from one of stainless steel, tantalum, platinum, a radiopaque material, a nickel-titanium alloy, a martensitic alloy, and a plastic.

11. A surgical clip according to claim 8, wherein:
said retainer portion has a length substantially 0.7 to 2 times the dimension between an outside of said first arm portion and an outside of said second arm portion.

12. A surgical clip, comprising:
a) a first arm portion;
b) a second arm portion;
c) a plurality of retainer portions located on one or more of said first and second arm portions and extending therefrom; and
d) a bridge portion connecting the first and second opposite ends,
wherein said first and second arm portions and said bridge portion are made from a single continuous piece of material and are substantially stiff to maintain a generally U-shaped configuration in which said first and second arm portions are substantially parallel to each other during application of said clip to tissue of the patient.

13. A surgical clip according to claim 12, further comprising:
e) at least one catch portion located on one or more of said first and second arm portions and adapted to engage at least one of said retainer portions.

14. A surgical clip according to claim 12, wherein:
at least one of said plurality of retainer portions is located on each of said first and second arm portions.

15. A surgical clip according to claim 12, wherein:
each said retainer portion extending from said first arm portion extends longitudinally beyond said second arm portion, and each said retainer portion extending from said second arm portion extends longitudinally beyond said first arm portion.

16. A method of applying a surgical clip to tissue, comprising:
a) providing a surgical clip having,
i) a first arm portion having a tip and a first opposite end,
ii) a second arm portion having a retainer extending therefrom in substantially the same direction as said second arm and a second opposite end, and
iii) a bridge portion connecting the first and second opposite ends,
wherein, said first and second arm portions and said bridge portion comprise a single continuous piece of material and are substantially stiff to maintain a generally U-shaped configuration in which said first and second arm portions are substantially parallel to each other before, during, and after application of said clip to tissue of the patient;
b) providing the first and second arm portions about the tissue; and
c) folding the retainer about the tip of the first arm while maintaining the first and second arm portions and the bridge portion in the generally U-shaped configuration.

17. A method according to claim 16, further comprising:
d) prior to providing the first and second arm portions about the tissue, compressing the tissue.
18. A method according to claim 17, further comprising:
e) providing a clip applier device, wherein said compressing the tissue is performed by said clip applier device.
19. A method according to claim 16, further comprising:
d) piercing the retainer through the tissue.

20. A method according to claim 16, wherein:
the tissue is non-tubular.
21. A method according to claim 16, wherein:
said folding the retainer includes plastically deformably bending said retainer substantially 180°.

* * * * *